US010996207B1

(12) United States Patent
Taheri

(10) Patent No.: US 10,996,207 B1
(45) Date of Patent: May 4, 2021

(54) SYSTEM AND METHOD TO MONITOR AND REPORT CONDITION OF A CONSUMABLE PRODUCT

(71) Applicant: Babak Taheri, San Francisco, CA (US)

(72) Inventor: Babak Taheri, San Francisco, CA (US)

( * ) Notice: Subject to any disclaimer, the term of this patent is extended or adjusted under 35 U.S.C. 154(b) by 102 days.

(21) Appl. No.: 16/278,124

(22) Filed: Feb. 17, 2019

Related U.S. Application Data

(63) Continuation-in-part of application No. 15/182,203, filed on Jun. 14, 2016, now abandoned.

(60) Provisional application No. 62/187,687, filed on Jul. 1, 2015.

(51) Int. Cl.
| | |
|---|---|
| *G01N 3/14* | (2006.01) |
| *B65D 51/24* | (2006.01) |
| *B65B 61/20* | (2006.01) |
| *G01N 21/27* | (2006.01) |
| *G01N 33/14* | (2006.01) |

(52) U.S. Cl.
CPC ......... *G01N 33/146* (2013.01); *B65B 61/202* (2013.01); *B65D 51/245* (2013.01); *B65D 51/248* (2013.01); *G01N 21/27* (2013.01)

(58) Field of Classification Search
CPC ...... G01N 33/146; G01N 21/27; G01N 21/65; G01N 21/9018; G01N 21/9036; B65B 61/202; B65D 51/245; B65D 51/248; G01F 23/292; G02B 26/101; A61B 5/076; G06Q 10/087
USPC ........................................................ 702/188
See application file for complete search history.

(56) References Cited

U.S. PATENT DOCUMENTS

| | | | | | |
|---|---|---|---|---|---|
| 2013/0314244 | A1* | 11/2013 | Hershberger | ..........| G01D 4/002 340/870.02 |
| 2015/0000371 | A1* | 1/2015 | Greene | ................ | G01N 33/146 73/19.1 |
| 2015/0307245 | A1* | 10/2015 | Puccini | .................. | B65D 41/02 215/228 |
| 2015/0355012 | A1* | 12/2015 | Gurumohan | ............. | H04Q 9/00 702/55 |
| 2016/0123876 | A1* | 5/2016 | Muldoon | ............. | G01N 33/146 356/338 |
| 2016/0138993 | A1* | 5/2016 | Van De Meulenhof | ..................... G01P 21/00 702/104 |

(Continued)

FOREIGN PATENT DOCUMENTS

WO    WO-2014198564 A1 * 12/2014 .............. G01W 1/18

*Primary Examiner* — Michael P Nghiem

(57) ABSTRACT

A system and method are provided to monitor, store and communicate data on parameters of a consumable product stored in a sealed container. In one embodiment, the method includes hermetically sealing the product in the container, and packaging the container for sale to a consumer. Packaging includes attaching a system to the container to monitor and store in the memory data on parameters of the consumable product. Attaching the system includes affixing a flexible substrate including a laser-detector pair directly to an outer surface of the container. The laser-detector pair is configured to pass laser light through the container to reflect from a reflector affixed to the outer surface of the container opposite the laser-detector pair to non-invasively sense parameters of the consumable product. The method further includes providing an interrogator to the consumer to communicate with the system to access the data.

18 Claims, 10 Drawing Sheets

(56) References Cited

U.S. PATENT DOCUMENTS

2016/0169796 A1\* 6/2016 Lewander Xu ........ G01N 21/61
356/437
2016/0223508 A1\* 8/2016 Angres ................ G01N 33/143

\* cited by examiner

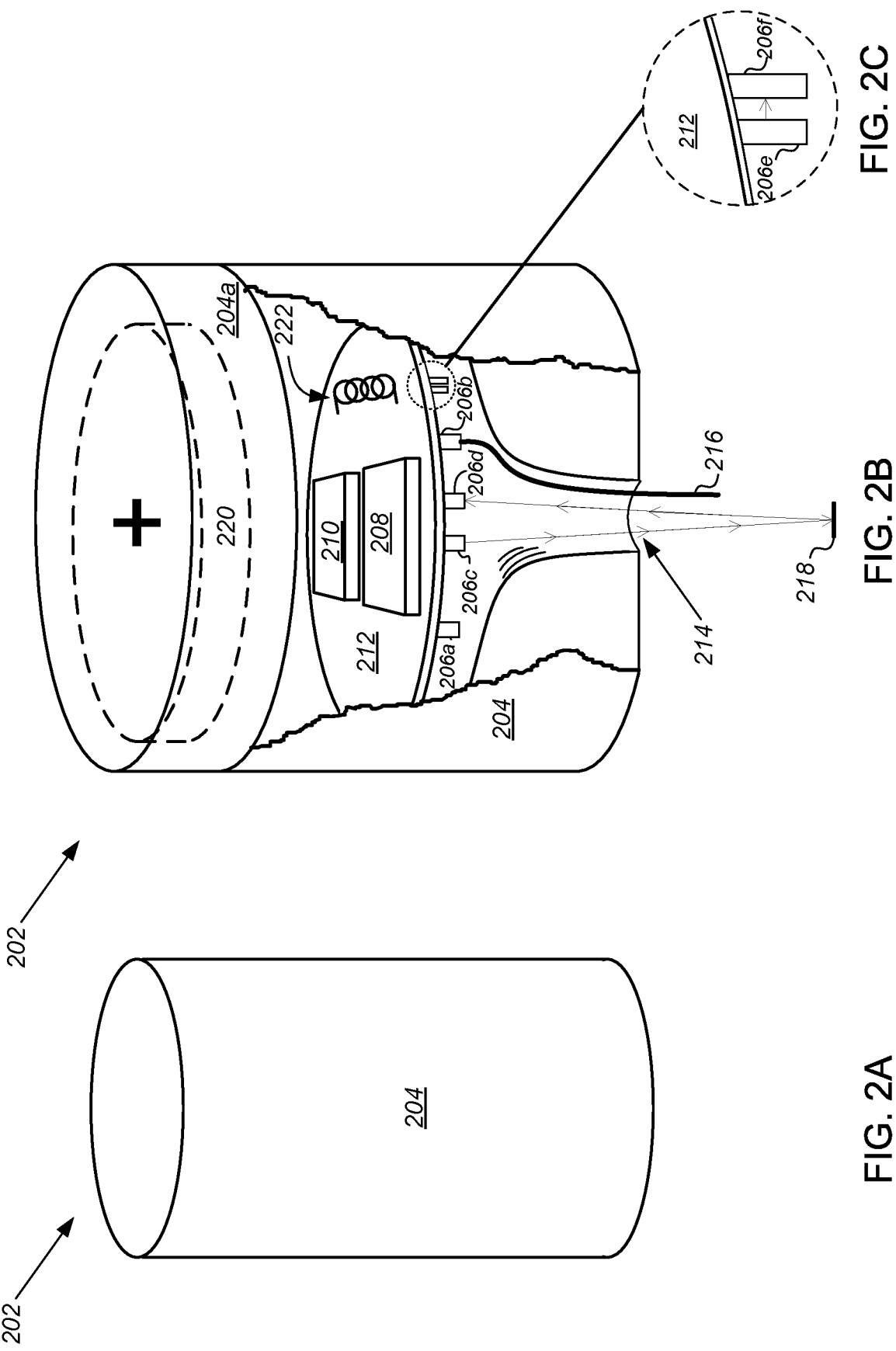

SYSTEM AND METHOD TO MONITOR AND REPORT CONDITION OF A CONSUMABLE PRODUCT

CROSS-REFERENCE TO RELATED APPLICATIONS

This application is a continuation-in-part of U.S. application Ser. No. 15/182,203, now abandoned, filed Jun. 14, 2016, which claims the benefit of priority under 35 U.S.C. 119(e) to U.S. Provisional Patent Application Ser. No. 62/187,687, filed Jul. 1, 2015, both of which are incorporated by reference herein in its entirety.

TECHNICAL FIELD

The present disclosure relates generally to a system and method to monitor and report conditions of a consumable product, and more particularly to an instrumented label, wrap or closure to sense, measure, digitally store and communicate data about a consumable product stored in a container.

BACKGROUND

Consumable products stored or transported within sealed containers are subject to degradation in quality over time arising both from chemical reactions occurring in the product or container, and environmental conditions, such as heat, cold, light, leakage, moisture or pressure, to which the container is exposed. For example, when white wine or red wine is exposed to air, the color of the wine changes. In aged wines, both white and red, this is natural and to be expected. But if wine is young (1 or 2 years old), it can be a sign that the wine has been exposed to too much air. This can either mean the bottle has been open for a few days or it may have happened in the winery or during the bottling with a poorly air sealed/defective bottle cork, or poorly sealed/defective wine tank.

Additionally, it is frequently desirable for a purchaser or consumer of the consumable product to be able to quickly and reliably identify or authenticate and track a manufacturer, manufacture date and manufacturing batch of the consumable product.

Thus, there is a need for a system and method to help monitor, store and communicate data on condition or parameters of a consumable product stored in a sealed container.

SUMMARY

In accordance with embodiments of the present invention a system including an apparatus, such as a label, wrap or closure in or on a container holding consumable product, such as a wine bottle, in a barrel, and/or fermentation tank, to monitor, store and communicate data on parameters of the consumable product is described.

In one embodiment, the method includes hermetically sealing the product in the container, and packaging the container for sale to a consumer. Packaging includes attaching a system to the container to monitor and store in the memory data on parameters of the consumable product. Attaching the system includes affixing a flexible substrate including a laser-detector pair directly to an outer surface of the container. The laser-detector pair is configured to pass laser light through the container to reflect from a reflector affixed to the outer surface of the container opposite the laser-detector pair to non-invasively sense parameters of the consumable product. The method further includes providing an interrogator to the consumer to communicate with the system to access the data.

In another embodiment, the system includes a processor, a memory, a connectivity means to outside, and a number of sensors coupled to the processor, the number of sensors including a first flexible substrate affixed directly to an outer surface of a neck of the container and including a first laser-detector pair configured to pass laser light through a headspace inside the container to reflect from a first reflector affixed to the outer surface of the neck of the container opposite the first laser-detector pair to non-invasively sense parameters of the consumable product including Trichloroanisole (TCA), and a second flexible substrate affixed directly to an outer surface of a body of the container and including a second laser-detector pair configured to pass laser light through the consumable product in the container to reflect from a second reflector affixed to the outer surface of the body of the container opposite the second laser-detector pair to non-invasively sense parameters of the consumable product including one or more of dissolved concentrations of oxygen, carbon dioxide, sulfur dioxide and TCA, and an interrogator configured to communicate with the system to access the data on parameters of the consumable product.

BRIEF DESCRIPTION OF THE DRAWINGS

Embodiments of the present invention will be understood more fully from the detailed description that follows and from the accompanying drawings and the appended claims provided below, where:

FIGS. 2A through 2C illustrate an apparatus including an intelligent enclosure also known as a cap, cork, or stopper according to an embodiment of the present disclosure;

DETAILED DESCRIPTION

The present disclosure is directed generally to a system and method to sense, monitor, store and communicate data on parameters of a consumable product stored in a container.

In the following description, for purposes of explanation, numerous specific details are set forth in order to provide a thorough understanding of the present invention. It will be evident, however, to one skilled in the art that the present invention may be practiced without these specific details. In other instances, well-known structures, and techniques are not shown in detail or are shown in block diagram form in order to avoid unnecessarily obscuring an understanding of this description.

Reference in the description to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment. The term to couple as used herein may include both to directly electrically connect two or more components or elements and to indirectly connect through one or more intervening components.

Figure 1:
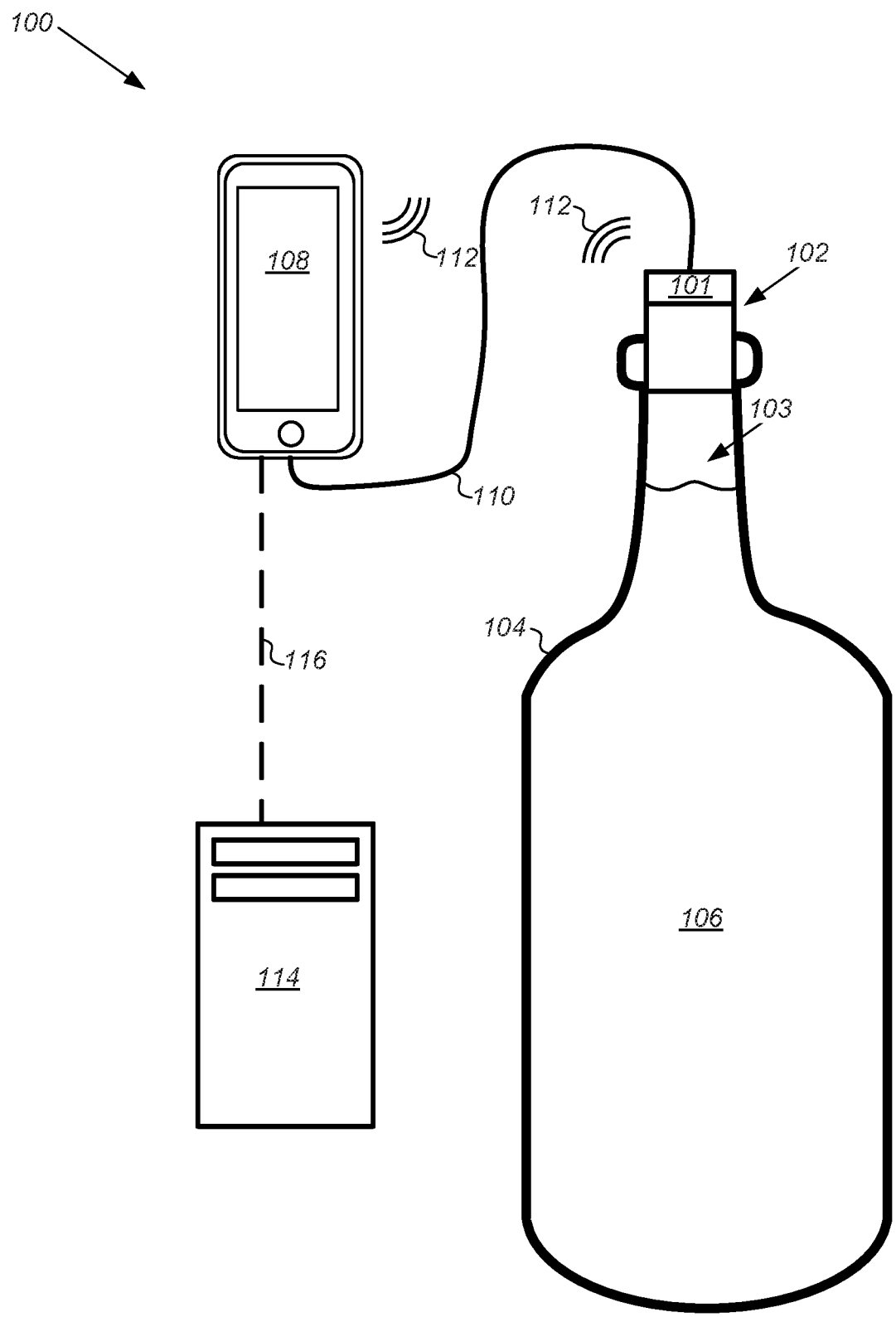
FIG. 1 is a block diagram of a system for sensing, monitoring, storing and communicating data on parameters of a consumable product placed in a container according to an embodiment of the present disclosure.

FIG. 1 illustrates a system 100 according to an embodiment of the present disclosure. Referring to FIG. 1 the system 100 includes an enclosure or apparatus 102 with a transponder 101 in or affixed to a container 104 holding a consumable product 106, and an interrogator unit 108 in wireless 112, or wired 110 communication or connectivity means with the apparatus 102. The apparatus 102 is adapted or configured to measure and store data on a number of parameters of the consumable product 106 in the container 104. Parameters include, but are not limited to, information used to identify and track a manufacturer, manufacture date and manufacturing batch of the consumable product 106, age, temperature history, Acetic Acid level, pH history, Carbon Dioxide ($CO_2$), dissolved oxygen ($O_2$) or total oxygen content of the container, pressure and/or sulfur dioxide ($SO_2$).

The interrogator unit 108 can be configured to communicate with the apparatus 102 through wired 110 or wireless 112 technologies. Examples of suitable wireless technology 112 include Near Field Communication (NFC), or Far Field Communication, such as Radio Frequency Identification (RFID). By Near field communication (NFC) it is meant a technology that enables wireless devices to establish radio communication with each other by touching the devices together or bringing them into proximity to a distance of typically 10 cm (3.9 in) or less. By Far Field communication (FFC) it is meant a technology that enables wireless devices to establish radio communication with propagating RF electromagnetic radiation through a space separating the devices, typically at a distance of 10 cm (3.9 in) or more.

Generally, the interrogator unit 108 is further configured or adapted to program the apparatus, including storing information on a manufacturer, manufacture date and manufacturing batch, calibrating the sensors, setting parameters to be sensed and measured, frequency of measurements, and alarm set points, and to read and/or display data received from the apparatus.

The interrogator unit 108 can include a mobile device such a cellular telephone, a tablet or notebook computer or a dedicated mobile device purpose made to communicate with the apparatus 102. Alternatively, the interrogator unit 108 can include a desktop computer or PC, a workstation or a control panel or system. It will be understood that this last embodiment is particularly advantageous where the container is not a single bottle of wine, but a cask or fermentation tank in a winery or hundreds to thousands of bottles of wine in a winery.

Optionally, as in the embodiment shown, the system 100 can further include or be connected to a remote processing, storage and analytics unit 114, such as a computer or server, through a wired and or wireless Internet Protocol (IP) network 116 for storing, analyzing and sharing of the data on the parameters to be sensed and measured, or a status of the system.

The apparatus 102 can further include or be formed in a closure used to seal the container 104, such as a cork, a screw on cap, or stopper, or integrally formed in or on a flexible substrate, such as a label or wrap affixed to the container. Embodiments of the apparatus 102 will now be described in greater detail with reference to FIGS. 2A through 8.

Referring to FIGS. 2A through 2C, in one embodiment the apparatus 202 further includes or is formed in a cork or stopper 204 placed in a container (not shown in this figure). The stopper generally includes a natural or synthetic material that is impermeable, elastic and non-reactive or compatible with the consumable product stored in a container. Suitable materials include, for example, cork, rubber and synthetic or man-made plastic or rubber compounds.

Referring to FIG. 2B, the apparatus 202 further includes housed within or attached to the stopper 204 a number of sensors 206, processor and support electronics 208, and a memory 210 coupled to the processor and support electronics. Preferably, as in the embodiment shown in FIG. 2B, the processor and support electronics 208 and memory 210 are fabricated on or mounted to a single substrate, such as a printed circuit board (PCB 212). Alternatively, in another embodiment (not shown), the memory 210 and processor and support electronics 208 can be integrally formed as a single integrated circuit (IC), such as a system on a chip, which is then attached to the PCB 212.

More preferably, as in the embodiment shown some of the sensors 206a, b, c, d, include components that are also fabricated on or mounted to the PCB 212 and positioned to sense conditions or parameters of the consumable product through an opening 214 in the stopper 204 to the container.

In one embodiment, one or more of the sensors 206b can be or can include a probe 216, such a thermocouple, electrodes, wire or a tube, which passes through the opening 214 into container. The probe 216 can be positioned so as to be at least partially immersed in the consumable product, or to be positioned in a headspace in the container. Referring to FIG. 1, by headspace 103 it is meant a volume left empty at a top of an almost filled container 104 before sealing.

In another embodiment, also shown in FIG. 2B the sensors can include one or more laser diodes or lasers 206c, such as each capable of generating different wavelengths and a detector such that when the laser light is emitted through opening 214 and reflected from the consumable product, or a reflective surface of the container itself, or a reflective surface or reflector 218 inside the container or a reflector affixed to an outer surface of a transparent container, the reflections are sensed by one or more detectors 206d. Changes in the reflected laser emissions can be used, for example, to measure color and other parameters, such as phenolics, gas and chemical content in wine.

Alternatively or additionally in yet another embodiment, shown in FIG. 2C, the sensors can include one or more lasers 206e, each capable of generating different wavelengths and positioned relative to one or more detectors 206f such that the laser light is passed through gases in the headspace and/or the content to detect and measure gases therein, such as, for example, sulfur dioxide ($SO_2$) and carbon dioxide ($CO_2$). Sulfur dioxide is commonly used as a preservative in bottling wine, and the presence and concentration of $SO_2$ can be used to indicate stability of a wine, i.e., whether or not it has been oxidized, and how it is developing. The presence and concentration of $CO_2$ can indicate whether or not the substance in the container has been a contaminated with a growing organism. In the embodiment shown in FIG. 2C, the laser 206e and detector 206f can be fixed to the circuit board 212 and positioned relative to one another so that the laser light is passed directly through the gases in the headspace, which enter through opening 214, to the detector. Alternatively, like the lasers 206c and detectors 206d described above the laser 206e and detector 206f can be configured and positioned to pass laser light through the opening 214 on to a reflector (not shown) in the headspace from which it is reflected back to the detector. Other types of sensor such as chemical field effect transistors (CHEMFETs) and/or Ion Sensitive Field Effect Transistors (ISFETS) can be used as sensors for gases and liquids. CHEMFETs are devices structurally similar to MOSFET transistors, in which the charge on a gate electrode is generated or applied by a chemical process in atoms, molecules, and ions in liquids and gases in contact with the CHEMFET. ISFETS are a particular type of CHEMFET used to detect ions in electrolytes.

The memory 210 is configured to store data on the sensed and measured parameters, and on the manufacturer, manufacture date and manufacturing batch of the consumable product stored in the container. Optionally, or preferably, the memory 210 is configured to store program information or code from the interrogator unit (not shown in this figure) including program code for calibrating the sensors 206, setting parameters to be sensed and measured, frequency of measurements, and alarm set points. The memory 210 can include read-only-memory (ROM), volatile or non-volatile random-access-memory (RAM) or a combination of all three. For example, the program code for calibrating the sensors 206, setting parameters to be sensed and measured, frequency of measurements, and alarm set points can be stored in an electrically erasable programmable read-only memory (EEPROM) that can be accessed only through the interrogator unit, while the data on the parameters of the consumable product sensed and measured by the apparatus 202 is stored in non-volatile memory, which enables data storage that is kept when no power is applied to the apparatus. The sensors 206 can be calibrated, for example, following assembling of the apparatus 202 prior to placement in a container by exposing the sensors to a known temperature, acidity or pH, $CO_2$ dissolved $O_2$ or $SO_2$ content, determining offsets or adjustment in gain necessary to calibrate sensors and storing this information or code in the memory 210. Alternatively, some of the sensors 206, such as temperature sensors, can be calibrated using a separate temperature sensor or thermometer external to the container with the assumption that the container and contents are at equilibrium. Other sensors 206, such as pH, $CO_2$, $O_2$ or $SO_2$ content can be calibrated using information provided by the producer of the consumable product, since it is often the change in these parameters over time that is of most concern.

The processor and support electronics 208 can include biasing circuits and power supplies, analog to digital converters (ADC), digital to analog converters (DAC), and calibration circuits to interface with the sensors 206 to measure and digitize the sensed parameters. It is noted that because been of the sensed parameters are monitored periodically and not continuously, many of the support electronics 208, such as ADCs and DACs can be shared, thereby reducing the cost and complexity of the apparatus 202 as well as power consumption.

In some embodiments, such as that shown, the apparatus 202 can further include a battery 220 to power the apparatus and store data in the memory 210 for many years. In one advantageous embodiment, shown in FIG. 2B, the battery 220 is housed in the stopper 204 and the stopper includes a removable cover 204a that enables the battery to be replaced without removing stopper from the container or exposing the consumable product stored therein to the environment.

Optionally, the apparatus 202 can be powered by a wired or wireless connection to the interrogator unit. In one version of this embodiment, described in greater detail below with reference to FIG. 3A, the apparatus 302 further includes one or more of the antennas 324, through at least one of which it collects energy by electromagnetic induction from radio waves produced by an interrogator unit.

Figure 3A:
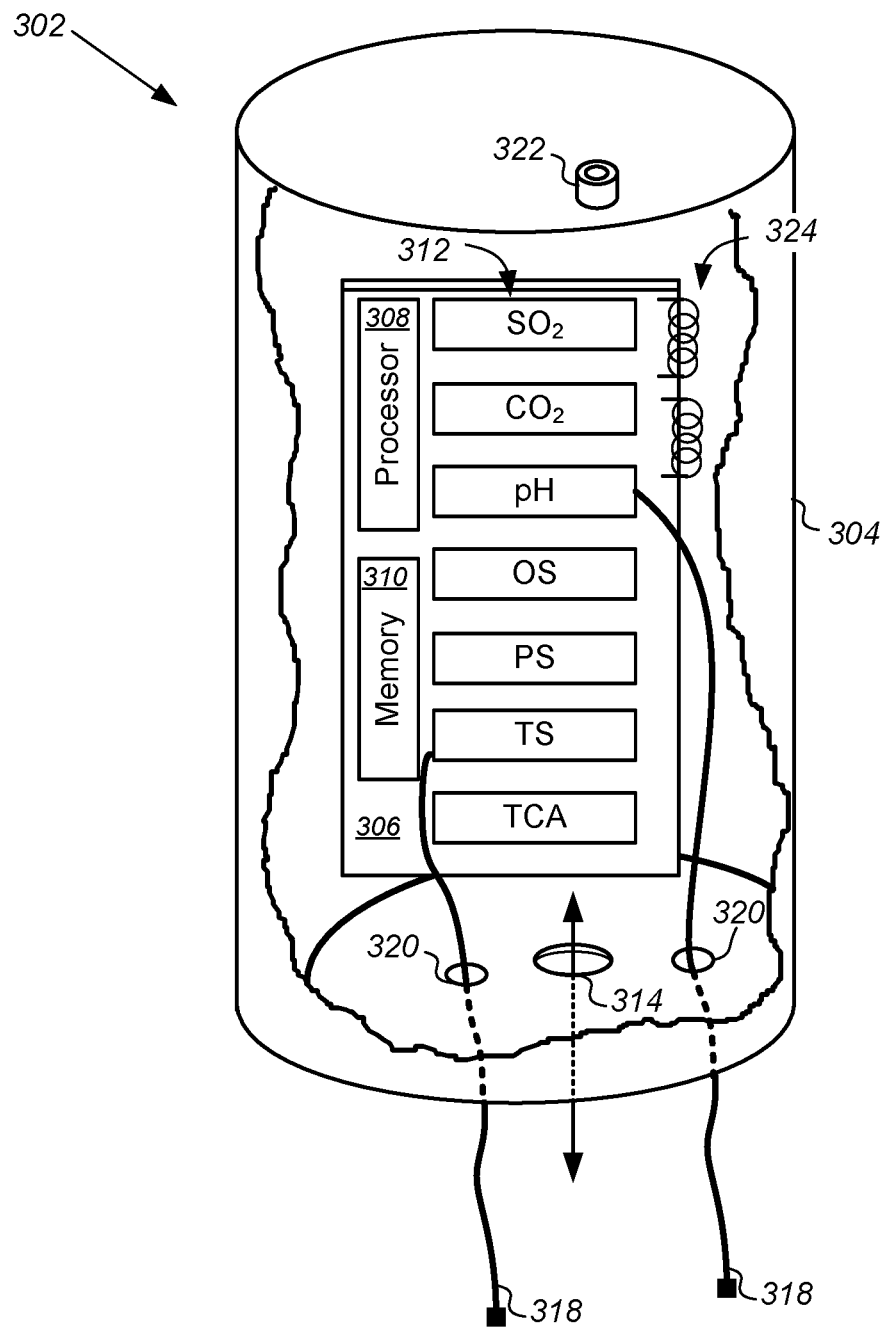
FIG. 3A illustrates an intelligent enclosure also known as a cap, cork, or stopper according to another embodiment of the present disclosure.
Figure 3C:
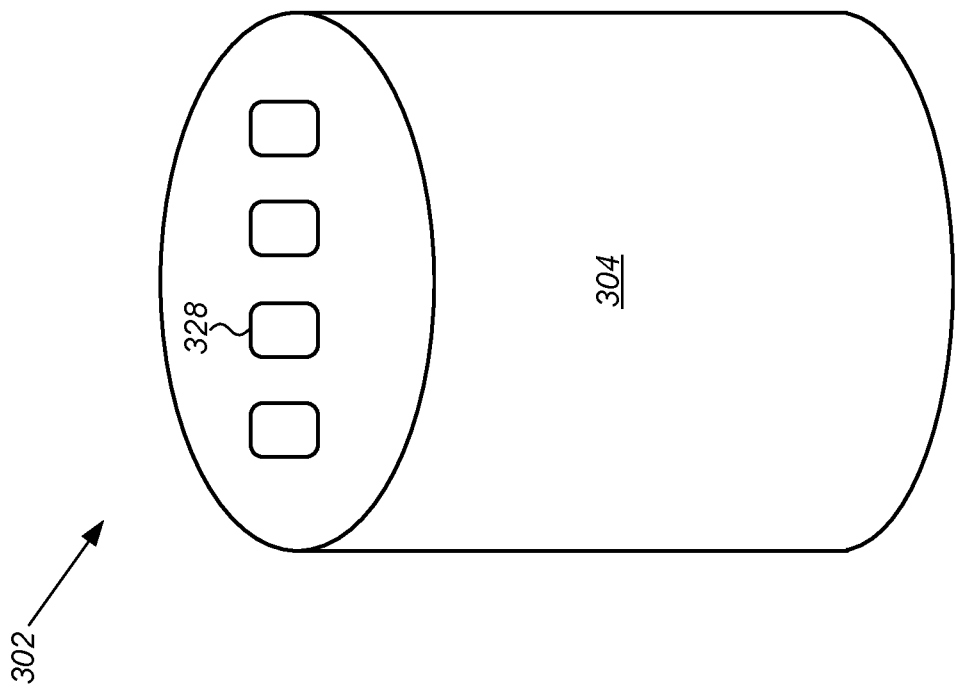
FIGS. 3B and 3C illustrate alternative embodiments of the intelligent closure of FIG. 3A.
Figure 3B:
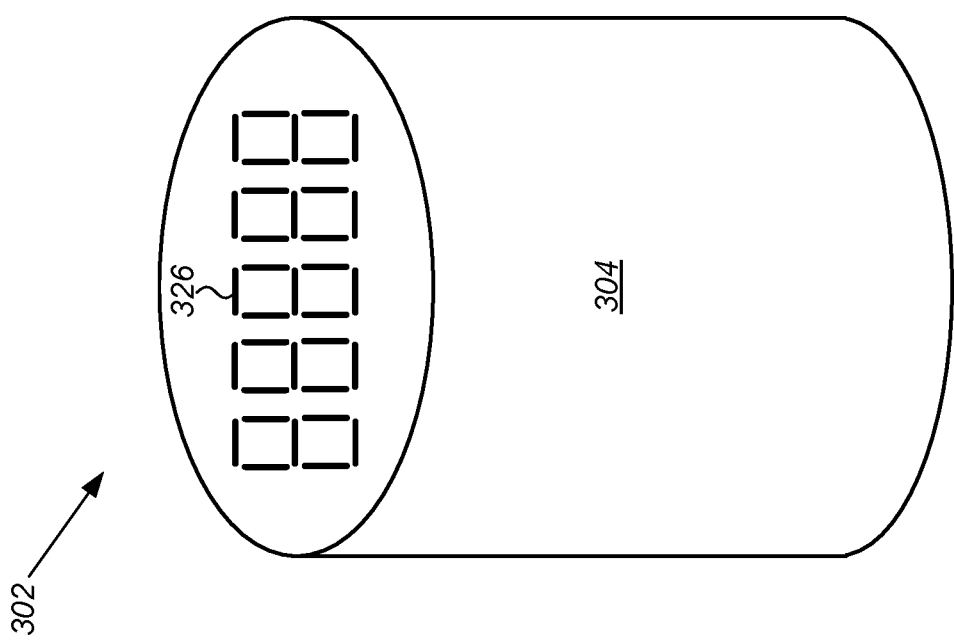

FIG. 3A illustrates an apparatus 302 including a stopper 304 according to another embodiment of the present disclosure. FIGS. 3B and 3C illustrate alternative embodiments of the closure 304 of FIG. 3A including different displays or means for displaying information regarding the sensed and measured parameters and/or on a status of the system.

Referring to FIG. 3A, the apparatus 302 includes a stopper 304 housing a PCB 306 to which are mounted processor/support electronics 308, a memory 310, and a number of sensors 312. Some of the sensors 312 are mounted to the PCB 306 and configured or adapted to sense conditions or parameters of the consumable product through an opening 314 in the stopper 304 through which gasses can pass to or from the container (as indicated by arrow 316). Others of the sensors 312 can include a probe 318, such a thermocouple, electrodes, wire or a tube, which passes through additional openings 320, which may or may not be sealed.

The sensors 312 can include a temperature sensor (TS), which can be either a contact or non-contact sensor. Contact temperature sensors measure the temperature of a device in contact with the consumable product or the container holding the consumable product. Thus, the temperature sensor can measure the temperature of the consumable product either by measuring the temperature of the consumable product directly or by measuring the temperature of the container in which it is stored therein, and inferring that the two are in thermal equilibrium, that is by assuming there is no heat flow between them. For example, in the case in which the consumable product is wine stored in a bottle, the temperature sensor can be in thermal contact with either the bottle or the wine. Suitable contact temperature sensor (TS) for such measurements includes thermocouples, thermistors, bi-metallic, heat flux sensor, resistive temperature detectors/Sensor (RTDs/RTSs), and silicon bandgap temperature sensors such as diodes and transistors.

Non-contact temperature sensors can provide the temperature of an object without being in direct contact to the object. Examples of such sensors are infrared thermometers, bolometers, laser/photo detector combination, and microwave sensors.

In either case a temperature sensor accuracy of about 0.5° C. is desirable for these applications. In addition the size and power consumption required for some applications lends itself to use a contact temperature sensor such as thermocouple, RTD or silicon bandgap sensor.

The sensors 312 can include a pressure sensor (PS) that measures pressure, typically of gases or liquids in the container. Pressure is an expression of the force required to stop a fluid from expanding, and is usually stated in terms of force per unit area. A pressure sensor usually acts as a transducer; it generates an electrical signal as a function of the pressure imposed. Pressure sensors can alternatively be called pressure transducers, pressure transmitters, pressure senders, pressure indicators, piezometers and manometers, among other names. Pressure sensors can vary drastically in technology, design, performance, application suitability and cost. Pressure sensors can be classified as absolute or differential sensors. Many technologies can be employed in making pressure sensors. Example of pressure sensors technologies are Piezoresistive strain gauge; Capacitive; Electromagnetic; Piezoelectric; Optical; Potentiometric; Resonant and thermal. Inside a sealed container, such as a bottle of wine the pressure of the headspace can be as high as 30 pounds-per-square inch (PSI). An increase in pressure of a sealed container can indicate a possibly undesired fermentation of the contents, while a decrease could indicate a failure of the seal.

The sensors 312 can also include pH sensors (pH) to sense how acidic or basic (alkaline) a consumable product stored in the sealed container is. The pH sensor (pH) measures values of a hydrogen ion concentration—which ordinarily ranges between about 1 and $10\times-14$ gram-equivalents per liter—into numbers between 0 and 14. On the pH scale a very acidic solution has a low pH value such as 0, 1, or 2 (which corresponds to a large concentration of hydrogen ions ($10\times0$, $10\times-1$, or $10\times-2$ gram-equivalents per liter), while a very basic solution has a high pH value, such as 12, 13, or 14 which corresponds to a small number of hydrogen ions ($10\times-12$, $10\times-13$, or $10\times-14$ gram-equivalents per liter). A neutral solution such as water has a pH of approximately 7. pH is an important parameter to be measured and controlled. For example, a low pH value can be a sign that acetic acid bacteria have been at work in your wine causing a fault known as volatile acidity (VA). A little bit of VA can add complexity and be a good thing, but when it dominates, it becomes a fault.

A pH sensor is generally made up of three components; (i) a combined electrode, which includes a measuring electrode, a reference electrode, and a temperature sensor; (ii) a preamplifier; and (iii) an analyzer or transmitter. The pH sensor essentially forms a battery where the positive terminal is the measuring electrode and the negative terminal is the reference electrode. The measuring electrode, which is sensitive to the hydrogen ion, develops a potential (voltage) directly related to the hydrogen ion concentration of the solution. The reference electrode provides a stable potential against which the measuring electrode can be compared. When immersed in the solution, the reference electrode potential does not change with the changing hydrogen ion concentration. A solution in the reference electrode also makes contact with the sample solution and the measuring electrode through a junction, completing the circuit.

The sensors 312 can further include one or more oxygen sensors (OS), such as an oxygen sensor to sense and measure oxygen concentration in the headspace, and a dissolved oxygen sensor to sense and measure a concentration of oxygen dissolved in the consumable product itself. Too much oxygen in the container or consumable product can lead to oxidation, which can destroy the flavor if not the nutritional value of the consumable product. For example, oxidized wines lose their brightness, both in color and in flavor. Bright reds turn to brick color or brownish and fresh tastes develop drier, bitterer characteristics. Knowing the history or the amount of oxygen in a bottle over time gives a good clue as the quality of wine one taste. Other parameters such as total package oxygen (TPO) is the head space plus dissolved oxygen is acceptable if only 1-2 mg/L. Knowing this fact, and the Oxygen Ingress (OI) known at bottling and the closure oxygen transfer rate, one can then estimate the aging trajectory of a wine. For example it is known that a TPO value of 2-12 ppm in bottling wines is equal to 1-3 years of preservation for a wine.

Oxygen sensors can include a zirconia, lambda sensor is based on a solid-state electrochemical fuel cell in which two electrodes provide an output voltage corresponding to the quantity of oxygen in the headspace or consumable product being measured relative to that in the atmosphere, or titania sensor that does not generate its own voltage, but changes its electrical resistance in response to the oxygen concentration.

The sensors 312 can further include a carbon dioxide ($CO_2$) sensor to sense and measure $CO_2$ concentration in the headspace, and/or dissolved $CO_2$ dissolved in the consumable product itself. $CO_2$ sensors can include nondispersive infrared gas sensors (NDIR) and chemical gas sensors. NDIR sensors are spectroscopic sensors that detect $CO_2$ in a gaseous environment by measuring a characteristic absorption of $CO_2$. The key components are an infrared source, a light tube, an interference (wavelength) filter, and an infrared detector. Chemical $CO_2$ gas sensors include $CO_2$ sensitive layers based on polymer- or heteropolysiloxane that react with $CO_2$ to change the optical or electrical properties of the layers.

The sensors 312 can further include a sulfur dioxide sensor ($SO_2$). This is particularly advantageous where the consumable product being monitored using the apparatus and method of the claimed invention is wine. Sulfur dioxide is used in wine for preservation and typically decreases as wine ages or goes bad. Thus, knowing the history of the amount of sulfur dioxide in a bottle over time gives a good clue as the quality of wine one taste. Free or gaseous $SO_2$ can vary from about 2 to 50 mg/liter or ppm, and is often the best indication of oxidation and how wine is developing. Anything below 10 ppm for white wine is bad.

Finally, the sensors 312 can further include a Trichloroanisole (TCA) sensor. Depending on the wine, an acetic acid (vinegar) sensor will indicate spoilage compound, as well as TCA. The pH sensor can detect acetic acid. Alternatively, the TCA sensor can be a dedicated sensor that detects TCA gases in the headspace through chemical sensors or absorbance or scattering of wavelengths of laser light passing through the headspace, i.e., gas chromatography.

In another embodiment, the sensors can include one or more laser diodes and detectors (such as lasers 206c, d and detectors 206e, f shown in FIG. 2B) with varying wavelengths that can be used to detect $CO_2$ but also phenolic compounds, color, and/or $SO_2$. Referring to FIG. 2B, the laser diodes and detectors can be positioned relative to one another and to a reflector 218 so that the detector receives a reflection of laser light passing through a liquid in the container, or only through gases in the headspace.

Referring again to FIG. 3A, it is noted that in some embodiments the apparatus may further include a connector or jack 322 through which the apparatus 302 can communicate by a wired communication to an interrogator unit (not shown in this figure). Optionally, the jack 322 may further serve as a port by means of which the apparatus 302 can be powered or to re-charge a battery (not shown in this figure) housed in the stopper 304.

Finally, the apparatus 302 may further include one of more antennas 324 through which the apparatus can wirelessly communicate with the interrogator unit. The wireless communication can include either Near Field Communication, or Far Field Communication, such as Radio Frequency Identification (RFID).

Optionally, one or more of the antennas 324 may further serve to power the apparatus by electromagnetic induction from magnetic fields produced near the interrogator unit. For example, in one embodiment wherein multiple apparatuses 302 are used in residential or commercial wine cellar, each apparatus may advantageously be powered through one antenna, eliminating or reducing the dependence on a battery to power the apparatus, but read out individually using communication through a separate antennal by a single interrogator unit able to distinguish each apparatus by a unique identifier or by a different frequency.

In another embodiment, the entire apparatus 302 may be or include and RFID system. An RFID system includes three components: an antenna or coil; a transceiver with decoder, i.e., RFID reader; and a transponder, i.e., RFID tag, programmed with unique information. In this embodiment, the RFID tag is the apparatus housed in the stopper 304, and the RFID reader is the interrogator unit. RFID tags are categorized as either active or passive. An internal battery typically powers active RFID tags. Passive RFID tags operate without a separate external power source and obtain operating power generated from the reader. Both active and passive RFID tags can be rewritten and/or modified. It will be understood that in an embodiment in which the apparatus 302 housed in the stopper 304 functions as a passive RFID tag, parameters are sensed, measured and stored only while the interrogator unit is actively in wireless communication with the apparatus 302. However, by using non-volatile memory 310, trends in changes of the parameters over time can still be tracked, and this embodiment, by eliminating the need for replacing or charging a battery, provides the ability to continue to operate over long periods of time, even a number of years, provided the apparatus is read on a regular basis.

In another embodiment, shown in FIG. 3B, the stopper 304, which houses the sensors, processing and power supply circuitry or elements described above, can further include a multi-digit or multi-character alphanumeric display 326 on the stopper 304, can output or display information on one or more of the sensed and measured parameters and/or the status of the system. Information on the status of the system can include, for example, power available in an internal battery, or failure of one or more sensors. Information on the parameters can include indication when one or more of the parameters, such as temperature or oxygen content; have exceeded a predetermined value or set point. The display 326 can be either continuously active, activated when the apparatus 302 is touched by a user, or active when the apparatus is brought within a field generated by the interrogator unit.

In alternative embodiment, shown in FIG. 3C, the stopper 304 can further include a number of light emitting diodes (LEDs) 328, which can output or display information on one or more of the sensed and measured parameters and/or the status of the system either by a color of the LED, a position or a LED relative to the remaining LEDs. As with the display 326 described above, the LEDs 328 can be either continuously lit or active, activated when the apparatus 302 is touched by a user, or active when the apparatus is brought within a field generated by the interrogator unit. For example, the LEDs 328 can include an LED coupled to a temperature sensing circuit that when interrogated by the interrogator unit or when the apparatus 302 is touched by the user illuminates with one color, for example red, when a predetermined maximum temperature has been exceeded, and another, for example green, or remains dark when the temperature has remained below the maximum temperature since the last interrogation.

Optionally or additionally, the stopper 304 can further include an audible device, such as a speaker or buzzer, to signal an out of set point parameter or condition of the system that requires attention by the user. For example, the audible device can provide an audible signal to indicate a failing internal battery, or failure of one or more sensors.

Figure 4:
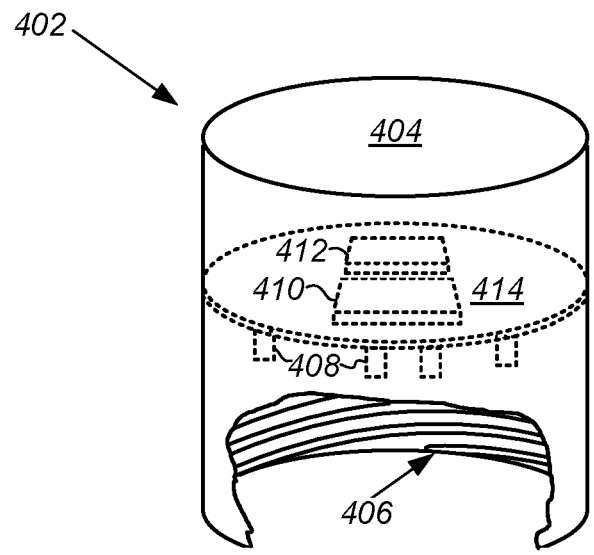
FIG. 4 illustrate an alternative embodiment of the apparatus in which the intelligent closure includes a threaded cap according to another embodiment of the present disclosure.

FIG. 4 illustrate an alternative embodiment of the apparatus 402 in which the intelligent closure includes a cap 404 having external or internal threads 406 to mate with threads on the container (not shown in this figure) sealing and affixing the apparatus to the container. As with the embodiments shown and described above with reference to the stoppers of FIGS. 2A and 3A, the apparatus 402 can further include housed within or attached to the cap 404 a number of sensors 408, a processor and support electronics 410, and a memory 412 mounted to a single substrate, such as a PCB 414 (shown in phantom in this figure). The sensors 408, processor and support electronics 410, memory 412 and PCB 414 can be configured as described in connection with FIG. 2A or 3A, and the apparatus 402 can be configured to communicate with the interrogator unit through wired or wireless technology.

In another embodiment, the apparatus is formed in or includes a flexible substrate affixed to the container in which the consumable product is held. In one version of this embodiment, illustrated in FIG. 5, the flexible substrate is a label that can further include printed information regarding the consumable product in the sealed container. In one version of this embodiment, illustrated in FIG. 6, the flexible substrate is a wrap, which can cover substantially all of the sealed container or a portion thereof. Optionally, the wrap can be affixed to the container in such a way as to provide assurance that a sealed closure in the container has not been tampered with.

Figure 5:
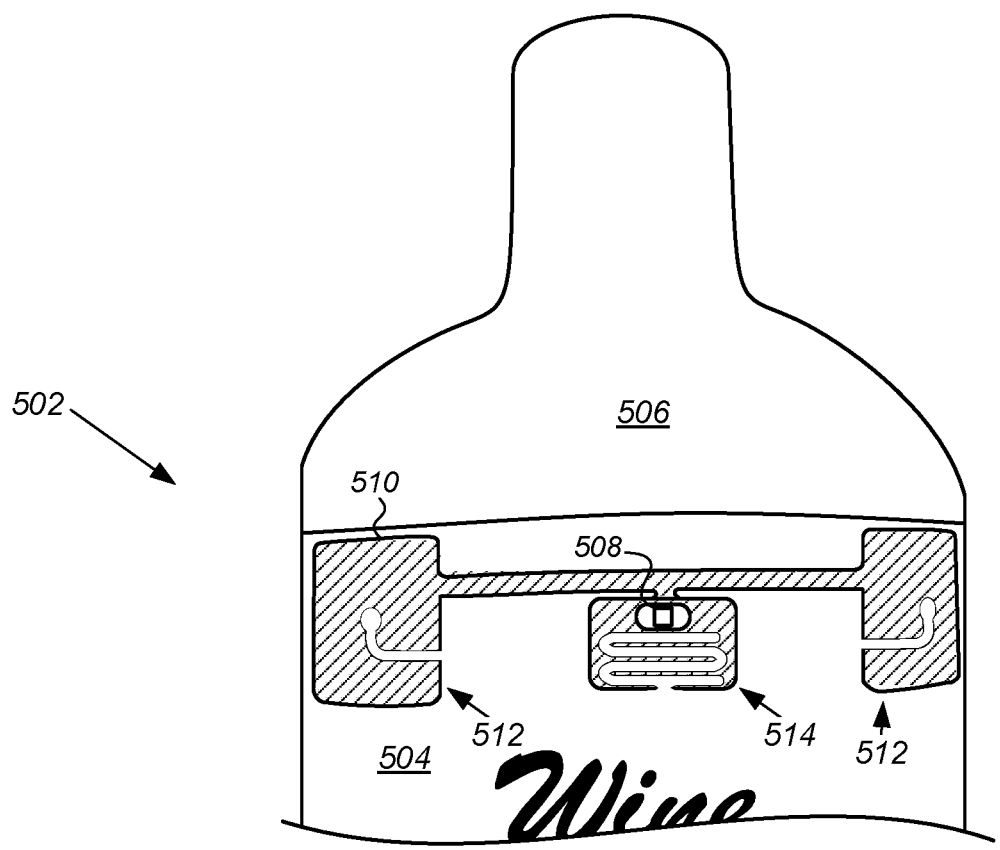
FIG. 5 illustrates an apparatus including an intelligent sensing label according to another embodiment of the present disclosure.

Referring to FIG. 5, in one embodiment the flexible substrate of the apparatus 502 is or includes a label 504 affixed to the container 506, an integrated circuit (IC 508) embedded in or attached to the label that includes a processor and support electronics, memory and, optionally, one or more sensors integrally formed in a single system on a chip (SOC). Preferably, as in the embodiment shown, the apparatus 502 further includes a thin layer of metal 510 or foil embedded in or attached to the label 504, which is configured to form one or more antennas 512 for communicating wirelessly with an interrogator unit and/or the apparatus by electromagnetic induction from radio waves produced by the interrogator unit, and to form a sensor 514, such as a contact temperature sensor to sense a temperature of the container. Optionally, in embodiments in which the IC 508 includes a laser and a detector, the layer of metal 510 may further include a reflector (not shown in this figure) to reflect laser emissions back towards the detector to measure color and other parameters, such as phenolics, gas and chemical content in wine.

Finally, it is noted that although the IC 508 and metal layer 510 are shown as exposed in FIG. 5, that need not be the case and label can be a laminate including the flexible substrate of the apparatus 502 covered by a decorative, dielectric layer, such as paper or a plastic, printed with information regarding the consumable product in the sealed container 506, such as a manufacturers name or trademark.

Figure 6B:
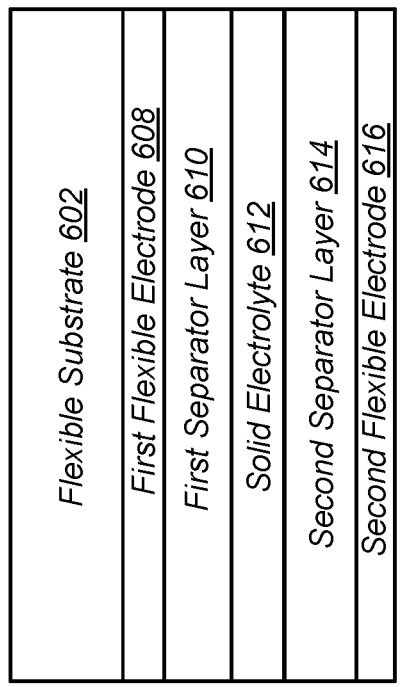
FIGS. 6A and 6B illustrate embodiments of a flexible substrate including a flexible battery for use with the embodiments of FIGS. 5 and 7.
Figure 6A:
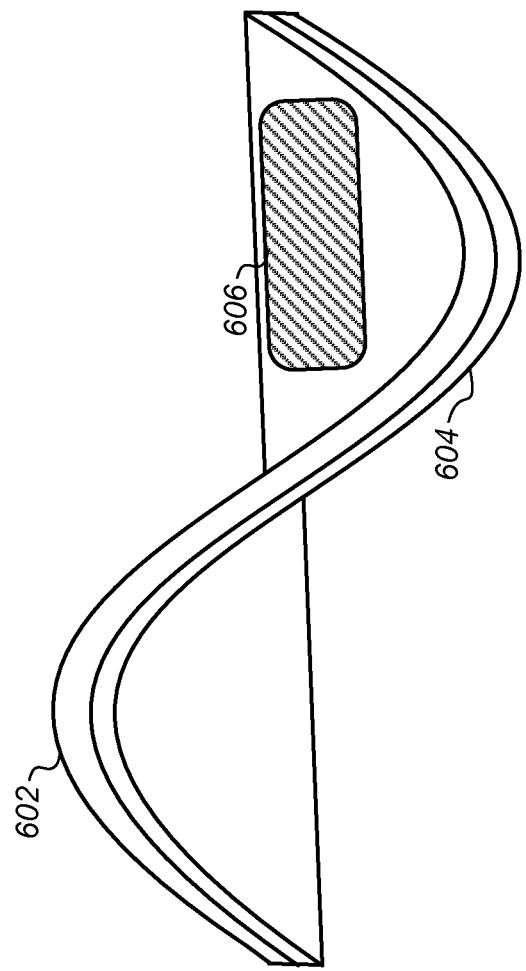

Alternatively or additionally in yet another embodiment the apparatus 502 further includes a thin film battery consisting of a cathode, anode, and separator layers printed one on top of another on the flexible substrate of the label 504. In one embodiment, shown in FIGS. 6A and 6B, the flexible substrate 602 is or includes a flexible battery 604, and the antenna and metal layers 606 substrate of the apparatus are formed on the flexible substrate. Generally, layers of the flexible battery 604 are formed over the flexible substrate 602 in a manner similar to the way in which ICs are constructed, and then the antenna and metal layers 606 are formed on a top or opposite surface of the flexible substrate. Layers of the flexible battery 604 are shown in detail in FIG. 6B. Referring to FIG. 6B, the flexible battery 604 generally include a first flexible electrode 608, such as a cathode or anode, formed on the flexible substrate 602, a first separator layer 610 formed on the first flexible electrode, a solid electrolyte 612 formed on the first separator layer, a second separator layer 614 formed on the solid electrolyte, and a second flexible electrode 616 formed on the second separator layer. The flexible substrate 602 can include a thermoplastic polymer, such as Polyethylene terephthalate (PET). The first and second flexible electrodes 608, 616, can include a thin layer of metal, such as gold or chromium. The solid electrolyte 612 can include a composite Li+-ion solid electrolyte. The separator layers 610, 614, can include a nanoporous polymer or carbon nanotubes.

Figure 7:
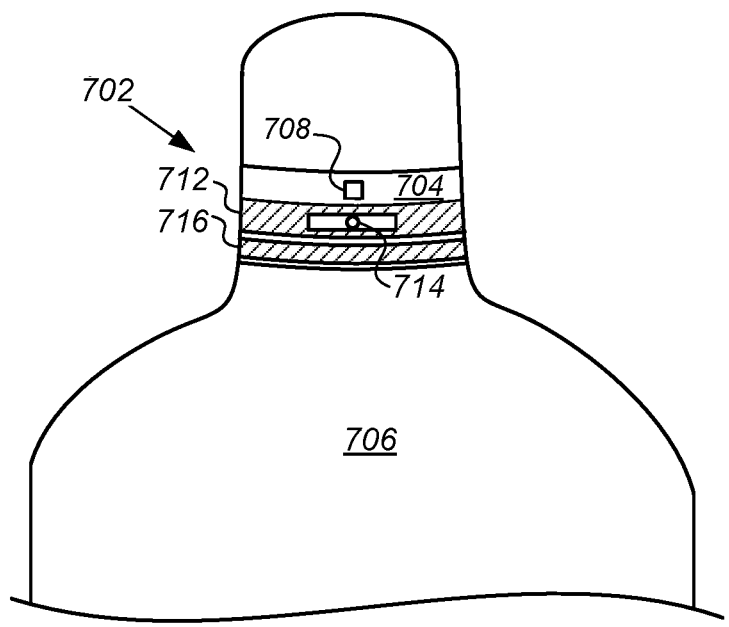
FIG. 7 illustrates an apparatus including an intelligent wrap according to another embodiment of the present disclosure.

Referring to FIG. 7, in another embodiment the flexible substrate of the apparatus 702 is or includes a wrap 704 affixed to the container 706, an IC 708 embedded in or attached to the wrap that includes a processor and support electronics, memory and, optionally, one or more sensors integrally formed in a single system on a chip or (SOC). The wrap 704 differs from the label 504 primarily in the location and extent to which it covers the container 706. In the embodiment shown in FIG. 7 the wrap is located on a neck of a sealed container 706, such as a wine bottle, and generally covers a much smaller area. In one advantageous embodiment, the wrap 704 is affixed to the neck of a wine bottle after the bottle has been sealed by a stopper covered by foil or a muselet so that the wrap overlays at least part of the foil or a muselet tamper to provide assurance that wine in the bottle has not been tampered with.

As with the label 504, the wrap 704 can, as in the embodiment shown, further include a thin layer of metal 712 or foil embedded in or attached to the wrap, which is configured to form one or more antennas for communicating wirelessly with an interrogator unit and/or the apparatus by electromagnetic induction from radio waves produced by the interrogator unit, and to form a sensor 714, such as a contact temperature sensor to sense a temperature of the container. In the embodiment shown, the apparatus 702 further includes a thin film battery 716 consisting of a cathode, anode, solid electrolyte and nanoporous separator layers printed one on top of another on the flexible substrate of the wrap 704.

Optionally, in embodiments in which the IC 708 includes a laser and a detector, the layer of metal 712 may further include a reflector (not shown in this figure) to reflect laser emissions back towards the detector.

Figure 8:
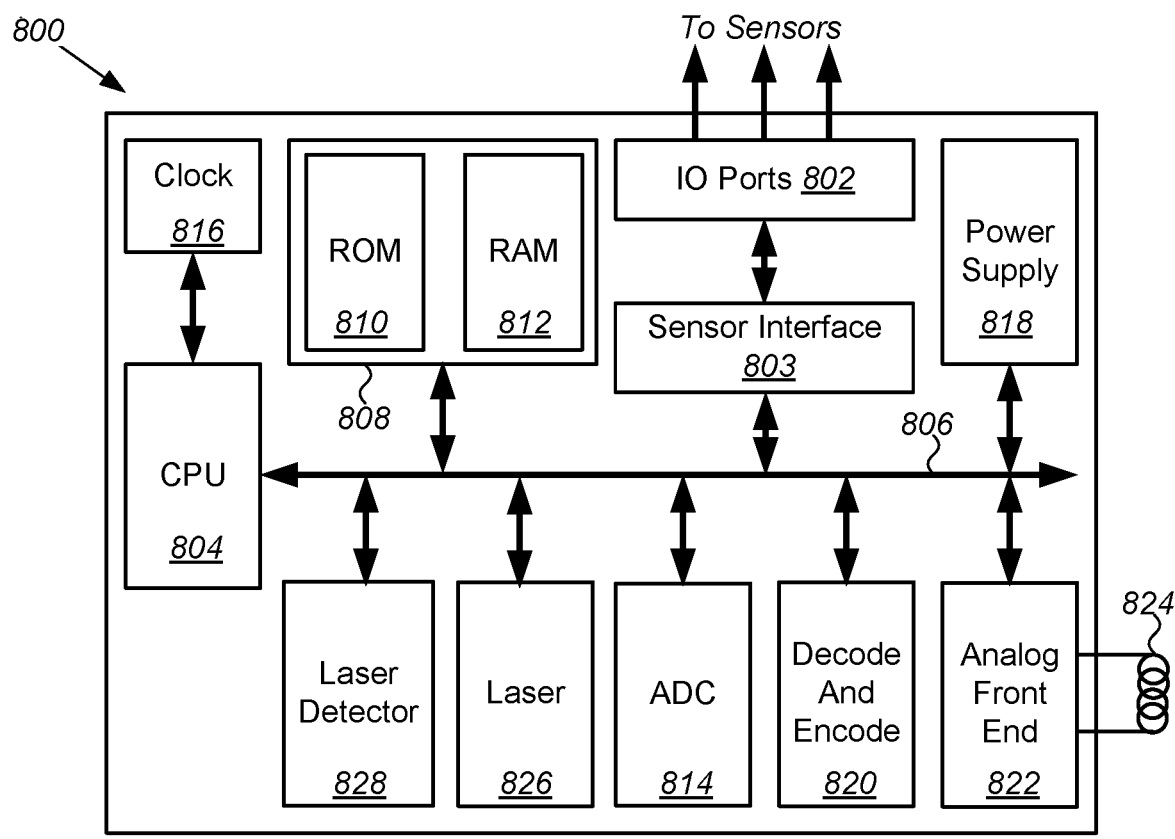
FIG. 8 is a block diagram of an embodiment of processor and support electronics, memory and sensors interface integrally formed on a single chip that is particularly useful with the intelligent label and the intelligent wrap of FIGS. 5 and 7.

FIG. 8 is a block diagram of an embodiment of processor and support electronics, memory and sensors integrally formed in single IC 800 or chip that is particularly useful with the label and wrap of FIGS. 5 and 7. Referring to FIG. 8 the IC 800 includes a number of input/output or IO ports 802 through which it is coupled to a number of sensors, such as the temperature sensors 514 or 714 shown in FIGS. 5 and 7; a sensor interface or conditioning circuit 803; a central processing unit (CPU 804) coupled to the IO ports through a bus 806 to receive signals from the sensors and process them to generate measurements that are stored in memory 808. As shown in FIG. 8, preferably the memory 808 includes read-only-memory (ROM 810) for storing the program code for calibrating the sensors, setting parameters to be sensed and measured, frequency of measurements, and alarm set points that can be accessed through the interrogator unit, and random-access-memory (RAM 812) in which parameters of the consumable product sensed and measured by the apparatus is stored. More preferably, the RAM 812 includes non-volatile memory that enables data storage when no power is applied to the apparatus.

Generally the IC 800 further includes a number of internal analog-to-digital converters (ADC 814) to convert an analog signal from the sensors to a digital signal for processing by the CPU 804, a clock 816 to synchronize and set an operating frequency for the IC, and a power supply 818 to supply power to the IC and sensors coupled thereto. Preferably, as in the embodiment shown, the IC 800 further includes a decode and encode circuit 820 and analog front end 822 coupled to an antenna 824 to enable wireless communication between the apparatus and an interrogator unit. Optionally, the analog front end 822 and the antenna 824 may be configured to serve to power the apparatus by electromagnetic induction from magnetic fields produced near the interrogator unit.

Alternatively or additionally in yet another embodiment the IC 800 may further include a laser 826 known to those skilled in the art as chip on wafer attachment (CoW), or die on wafer (DoW) attachment and a laser detector 828 to measure parameters of the consumable product, such as color, phenolics, gas and chemical content in wine. Generally, the laser 826 can include any suitable semiconductor laser capable of being integrally formed on a common substrate with the other circuits of the IC 800. For example, in one embodiment the laser 826 can include a vertical-cavity surface-emitting laser (VCSEL). Similarly, the laser detector 828 can include any suitable photosensor or photodetector capable of being integrally formed on a common substrate with the other circuits of the IC 800. Suitable technologies for the detector 828 include photodiodes, photoresistors, phototransistors and charge-coupled-devices (CCD).

Figure 9:
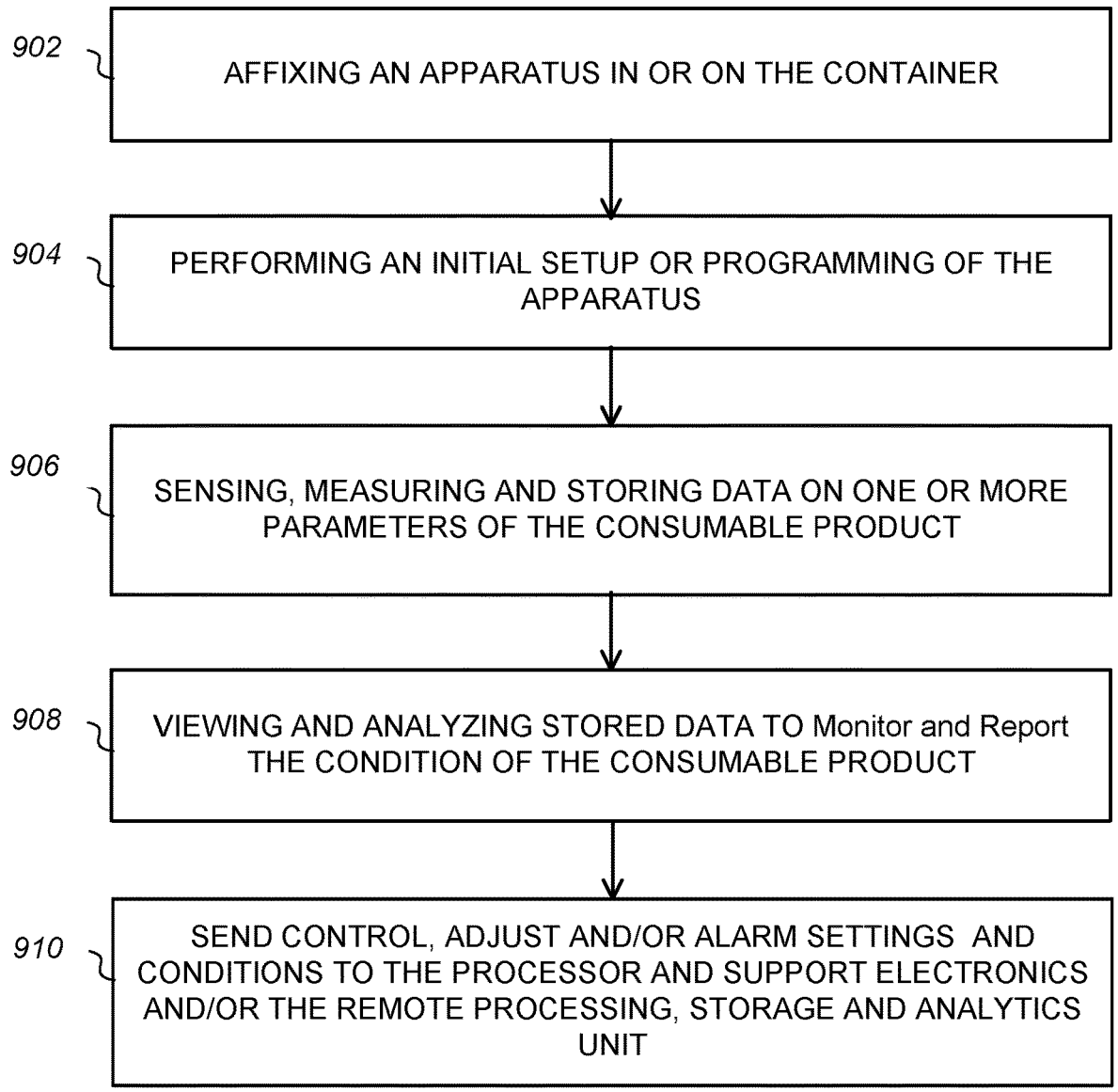
FIG. 9 is a flowchart illustrating a method for monitoring a parameter of a consumable product according to an embodiment of the present disclosure.

FIG. 9 is a flowchart illustrating a method for monitoring a condition of a consumable product in a sealed container according to one embodiment of the present disclosure. Referring to FIG. 9, the method begins with the affixing an apparatus according to an embodiment of the present disclosure in or on the container (902). Next, an initial setup or programming of the apparatus is performed (904). The initial setup or programming can accomplished, for example, by wired or wireless communication with an interrogator unit or by a remote processing unit connected through an IP network, and can include calibrating sensors of the apparatus, setting parameters to be sensed and measured, setting frequency of measurements, and/or alarm set points. In some embodiments the initial setup can include storing in a memory of the apparatus data or information on the manufacturer, manufacture date and manufacturing batch of the consumable product stored in the container. Thereafter, one or more parameters of the consumable product are sensed, measured and data on the resultant measurements stored in the memory of the apparatus in accordance with the initial setup or programming (906). Next, the data can be viewed or analyzed by a user using the interrogator remote processing unit to monitor the condition of the consumable product (908). Finally, control, adjust and/or alarm settings and conditions can be sent to the processor and support electronics and/or the remote processing, storage and analytics unit (910).

Figure 10:
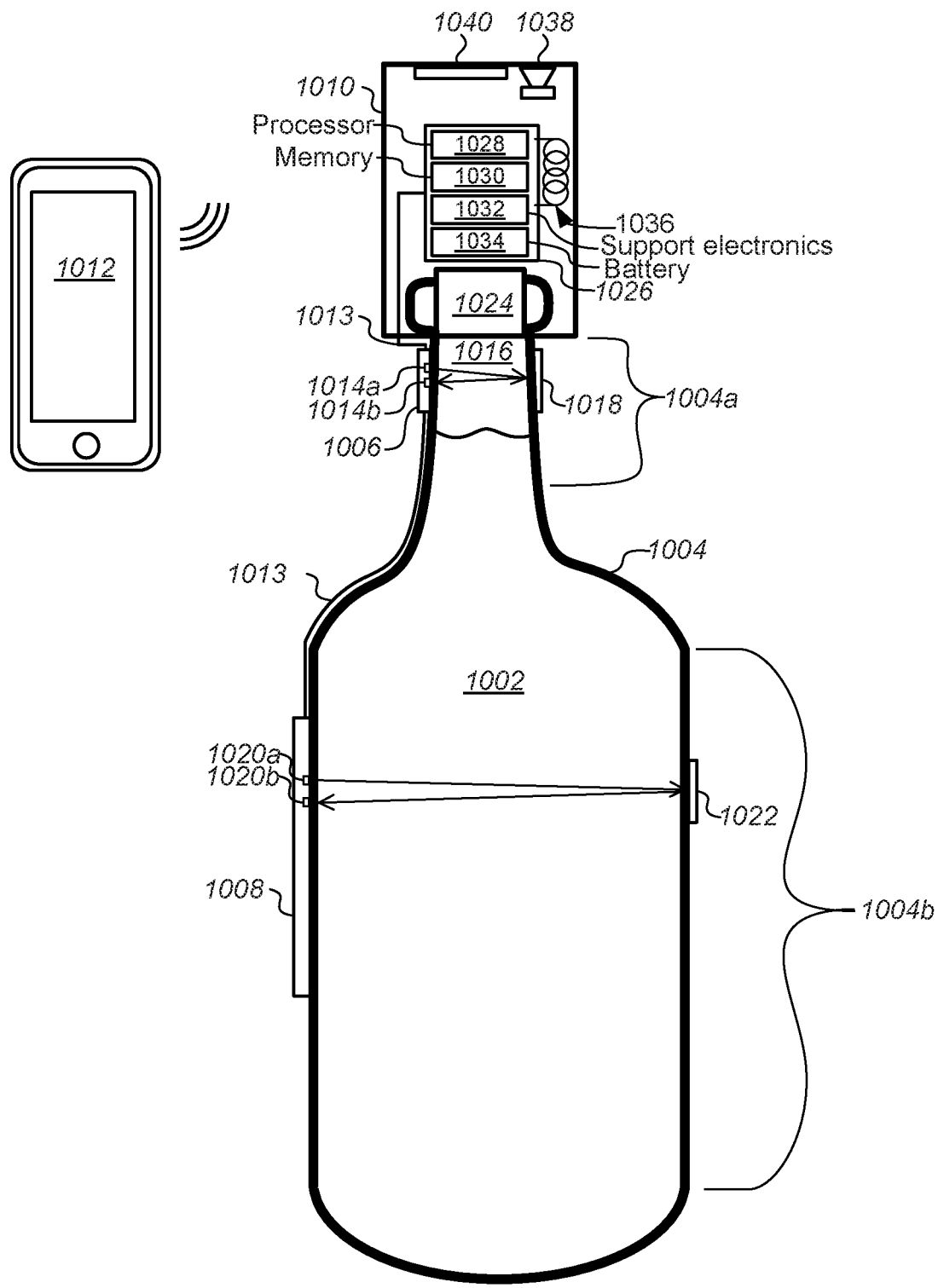
FIG. 10 is a block diagram of a system for sensing, monitoring, storing and communicating data on parameters of a consumable product in a container including the intelligent label and the intelligent wrap of FIGS. 5 and 7, and the cap of FIG. 3.

In another embodiment, shown in FIG. 10, the apparatus or system for sensing, monitoring, storing and communicating data on parameters of a consumable product 1002 in a container 1004 that is particularly suitable for use or placement by a producer or manufacturer when packaging the consumable product. Referring to FIG. 10 in the system can include an intelligent wrap 1006, such as that shown and described in connection with FIG. 7, an intelligent label 1008, such as that shown and described in connection with FIG. 5, and an intelligent cap 1010, such as that shown and described in connection with FIGS. 1-4. Generally, the system further includes an interrogator 1012 in wireless, or wired communication or connectivity means with the intelligent wrap 1006, intelligent label 1008 or intelligent cap 1010. Preferably, as in the embodiment shown the intelligent wrap 1006, intelligent label 1008 and intelligent cap 1010 are electrically connected through a thin or conductive film 1013, through which power and signals can be conducted.

The intelligent wrap 1006 includes a first flexible substrate affixed directly to an outer surface of a neck portion or neck 1004*a* of the container 1004. The intelligent wrap 1006 includes at least a first laser detector pair 1014*a*, 1014*b*, configured to pass laser light through a headspace 1016 inside the container 1004 to reflect from a first reflector 1018 affixed to the outer surface of the neck of the container opposite the first laser-detector pair to non-invasively sense parameters of the consumable product including one or more of oxygen, carbon dioxide, sulfur dioxide and Trichloroanisole (TCA). The reflector 1018 is preferably formed on the same flexible substrate as the first laser detector pair 1014*a*, 1014*b*. Because the light emitted by the laser 1014*a* is reflected it passes through the headspace 1016 twice before being received or detected by the detector 1014*b*, thereby improving the accuracy and sensitivity of the measurements. In a preferred embodiment, laser detector pair 1014*a*, 1014*b*, is capable of emitting and detecting a number of different wavelengths to sense and measure one or more of oxygen, carbon dioxide, sulfur dioxide and TCA in the headspace 1016. A processor in the system can control the laser detector pair 1014*a*, 1014*b*, to operate at different wavelengths at different times to sense and measure different substances, or as selected by the producer or purchaser of the a consumable product 1002.

The laser detector pair 1014*a*, 1014*b*, can sense the presence and measure the concentration of these elements or substances though either absorption or scattering of particular wavelengths of light emitted by the laser 1014*a*, which results in attenuation in the reflected light received by the detector 1014*b*. For example, laser detector pair 1014*a*, 1014*b*, can sense and measure the presence of TCA through absorption when operated at NIR wavelengths of from about 2.5 to 25 µm. Optionally, the wavelengths at which the laser detector pair 1014*a*, 1014*b*, operate are selected not only to detect and measure the presence of certain substance in the headspace, but may also be selected so that the container 1004 is substantially transparent to these wavelengths.

In addition to the laser detector pair 1014*a*, 1014*b*, the flexible substrate of the intelligent wrap 1006 can further include one or more of an antenna, a flexible battery and an IC embedded in or attached to the wrap that includes a processor and support electronics, memory and, optionally, one or more sensors, all as described above with reference to FIGS. 6 and 7.

The intelligent label 1008 includes a second flexible substrate affixed directly to an outer surface of a body portion or body 1004*b* of the container 1004. The intelligent label 1008 includes at least a second laser detector pair 1020*a*, 1020*b*, configured to pass laser light through the consumable product 1002 inside the container 1004 to reflect from a second reflector 1022 affixed to the outer surface of the neck of the container opposite the second laser-detector pair to non-invasively sense parameters of the consumable product including one or more of concentrations of dissolved oxygen, carbon dioxide, sulfur dioxide and TCA. The reflector 1022 is preferably formed on the same flexible substrate as the second laser detector pair 1020*a*, 1020*b*. Because the light emitted by the laser 1020*a* is reflected it passes through the consumable product 1002 twice before being received or detected by the detector 1020*b*, thereby improving the accuracy and sensitivity of the measurements. As with the intelligent wrap 1006, laser detector pair 1020*a*, 1020*b* of the intelligent label is preferably capable of emitting and detecting a number of different wavelengths to sense and measure one or more different substance or elements.

The second laser detector pair 1020*a*, 1020*b*, can also sense the presence and measure the concentration of these elements or substances though either absorption or scattering of particular wavelengths of light emitted by the laser 1020*a*, which results in attenuation in the reflected light received by the detector 1020*b*. For example, laser detector pair 1020*a*, 1020*b*, can sense and measure the presence of TCA through absorption when operated at NIR wavelengths of from about 2.5 to 25 µm. As with the intelligent wrap 1006, the wavelengths at which the second laser detector pair 1020*a*, 1020*b*, of the intelligent label 1008 operate can be selected not only to detect and measure the presence of certain substance in the consumable product 1002, but also so that the container 1004 is substantially transparent to these wavelengths.

Finally, in addition to the laser detector pair 1020*a*, 1020*b*, the flexible substrate of the intelligent label 1008 can further include one or more of an antenna, a flexible battery and an IC embedded in or attached to the label that includes a processor and support electronics, memory and, optionally, one or more sensors, all as described above with reference to FIGS. 5 and 6.

Referring to FIG. 10, the intelligent cap 1010 can include a cap removably attached over a closure or stopper 1024 used to hermetically seal the consumable product in the container 1004, as in the embodiment shown. Alternatively, the intelligent cap 1010 can include an intelligent cork or threaded closure, such as shown in FIGS. 3A and 4, used to hermetically seal the consumable product 1002 in the container 1004.

Generally, the intelligent cap 1010 includes a PCB 1026 to which are mounted a processor 1028, a memory 1030, and support electronics 1032. As in the embodiment shown, the intelligent cap 1010 can further include a battery 1034 and/or one or more of antennas 1036 through one of which it collects energy by electromagnetic induction from radio waves produced by an interrogator. Optionally, the intelligent cap 1010 can include further include an number of sensors (not shown) through which it can sense and monitor a number additional environmental conditions to which the container 1004 is exposed and that may impact the consumable product 1002, such as temperature, humidity, vibration or shock.

The interrogator unit or interrogator 1012 can include a mobile device such a cellular telephone, a tablet or notebook computer or a dedicated mobile device purpose made to communicate with the system. In one particularly advantageous embodiment for a system installed by a producer or manufacturer as part of packaging the product, the interrogator 1012 includes a software application or app, capable of being executed on a programmable electronic device, such a cellular telephone, and which software application the producer or manufacturer provides to the to the purchaser or consumer of the packaged consumable product 1002 to enable the consumer to access the data on parameters of consumable product monitored and stored by the system. Generally, the interrogator 1012 is further configured or adapted to program the system, including storing information on a manufacturer, manufacture date and manufacturing batch, calibrating the laser detector pairs and other sensors, setting parameters to be sensed and measured, frequency of measurements, and alarm set points.

Optionally, as in the embodiment shown and described in connection with FIGS. 3B and 3C the cap 1010 can further include a signaling means to communicate data or information on parameters of the consumable product by an audible 1038 or visible 1040 signaling device.

Figure 11:
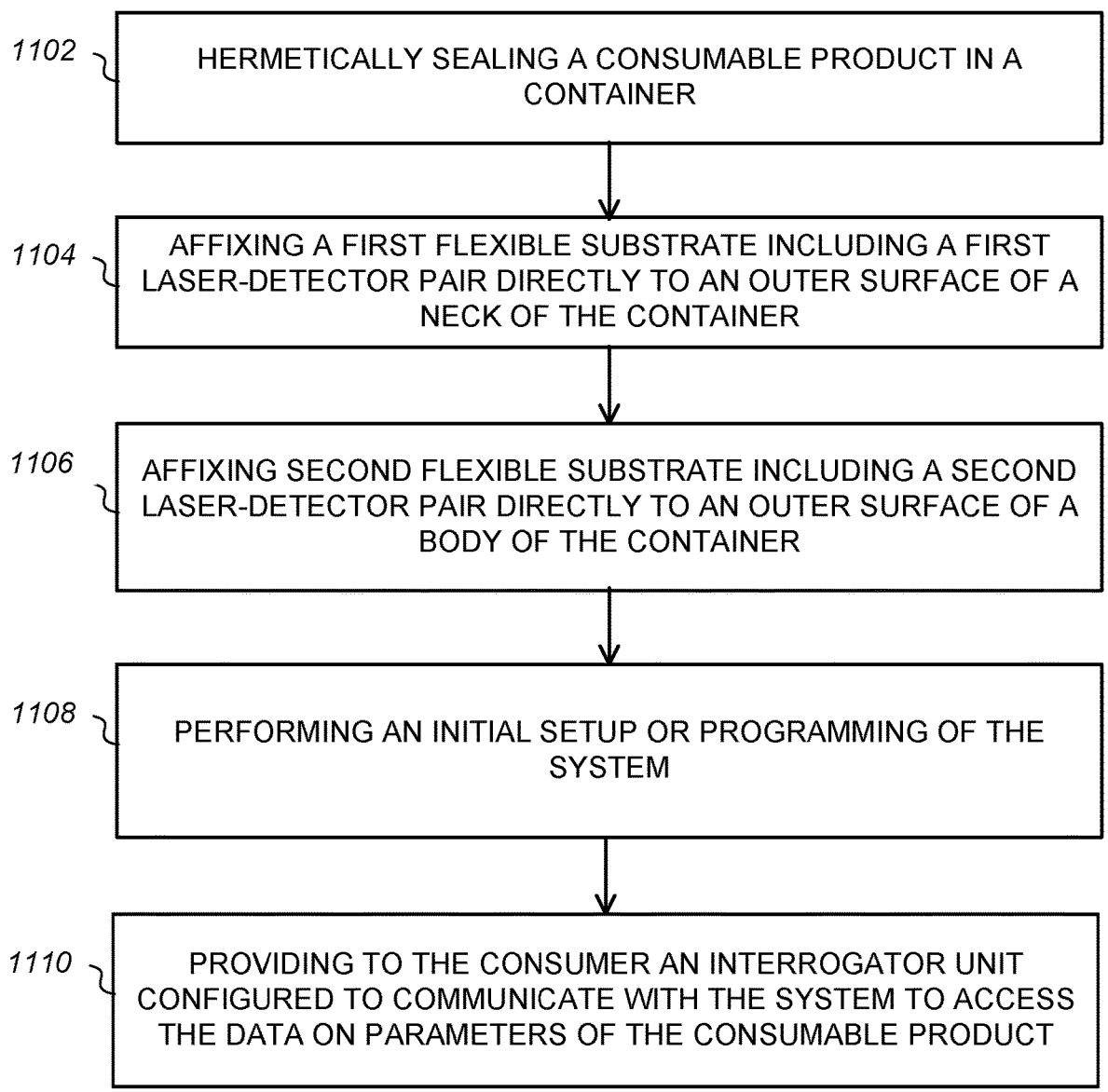
FIG. 11 is a flowchart illustrating a method for sealing a product in a container, and packaging the container for sale to a consumer including attaching a system for sensing, monitoring, storing and communicating data on parameters of the product in the container.

A method for sealing a product in a container, and packaging the container for sale to a consumer including attaching a system, such as that shown in FIG. 10, will now be described with reference to FIG. 11. Referring to FIG. 11, the method begins with a producer or manufacturer hermetically sealing a consumable product in a container (1102). As explained above, this can be accomplished with a conventional seal or stopper, such as a cork or screw on cap, over which an intelligent cap, such as that shown in FIG. 3B or 3C, containing part of the system can optionally be placed. Alternatively, the producer or manufacturer can hermetically seal the consumable product in the container using an intelligent cork, such as that shown in FIG. 3A, or a threaded, intelligent closure, such as that shown in FIG. 4.

Next, at least a first flexible substrate including a first laser-detector pair is directly affixed to an outer surface of the container (1104). Generally, the first flexible substrate is an intelligent label or wrap as described above with reference to FIGS. 5 and 7. In one embodiment, such as that shown in FIG. 10, the first flexible substrate is an intelligent wrap and the first laser-detector pair configured to pass laser light through a headspace inside the container to non-invasively sense parameters of the consumable product. Preferably, the method further includes the step of affixing a second flexible substrate including a second laser-detector pair directly to a body of the container to pass laser light through the consumable product as shown in FIG. 10, to non-invasively sense parameters of the consumable product (1106).

Next, an initial setup or programming of the system is performed (1108). As with the method described in FIG. 9, the initial setup or programming can be accomplished through a wired or wireless link between a programmable electronic device and a processor located in first flexible substrate (intelligent wrap), the second flexible substrate (intelligent label) or in an intelligent cap or closure covering or used in place of the conventional seal or stopper. The initial setup or programming can include calibrating the lasers and detectors of the first and second laser-detector pairs, setting parameters to be sensed and measured, setting frequency of measurements, and/or alarm set points. In some embodiments the initial setup can further include storing in a memory of the system data or information on the manufacturer, manufacture date and manufacturing batch of the consumable product stored in the container.

Finally, an interrogator configured to communicate with the system is provided to the purchaser or consumer of the packaged consumable product to enable the consumer to access the data on parameters of consumable product monitored and stored by the system (1110). Providing the interrogator to the consumer can include providing a software application capable of being executed on a programmable electronic device. In one embodiment, the programmable electronic device is a wireless communication device, such as a cellular telephone, and the software application provided to the consumer enables the wireless communication device to wirelessly communicate with the system.

Thus, embodiments of an apparatus or system and method to monitor, store and communicate data on parameters of a consumable product stored in a sealed container, have been described. Although the present disclosure has been described with reference to specific exemplary embodiments, it will be evident that various modifications and changes may be made to these embodiments without departing from the broader spirit and scope of the disclosure. Accordingly, the specification and drawings are to be regarded in an illustrative rather than a restrictive sense.

The Abstract of the Disclosure is provided to comply with 37 C.F.R. § 1.72(b), requiring an abstract that will allow the reader to quickly ascertain the nature of one or more embodiments of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Reference in the description to one embodiment or an embodiment means that a particular feature, structure, or characteristic described in connection with the embodiment is included in at least one embodiment of the circuit or method. The appearances of the phrase one embodiment in various places in the specification do not necessarily all refer to the same embodiment.

What is claimed is:

1. A method comprising:
    hermetically sealing a consumable product in a container;
    packaging the container before sale to a consumer, wherein said packaging comprises affixing directly to an outer surface of a neck of the container the container a first flexible substrate comprising a system including sensors, a processor and a memory to monitor and store in the memory data on parameters of the consumable product, wherein the sensors include a first laser-detector pair to pass laser light through a headspace inside the container to reflect from a first reflector affixed to the outer surface of the neck of the container opposite the first laser-detector pair to non-invasively sense parameters of the consumable product;

affixing directly to a body of the container a second flexible substrate including a second laser-detector pair to pass laser light through the consumable product in the container to reflect from a second reflector affixed to the outer surface of the body of the container opposite the second laser-detector pair to non-invasively sense parameters of the consumable product; and providing to the consumer an interrogator to communicate with the system to access the data on parameters of the consumable product.

2. The method of claim 1 wherein the parameters sensed using the first laser-detector pair include pH, oxygen, carbon dioxide, sulfur dioxide or Trichloroanisole (TCA).

3. The method of claim 1 wherein the first laser-detector pair emits and detects multiple, distinct wavelengths to sense oxygen, carbon dioxide, sulfur dioxide or Trichloroanisole (TCA) by gas chromatography.

4. The method of claim 1 wherein the first laser-pair emits and detects at least one wavelength that can pass through material of the container substantially without attenuation.

5. The method of claim 1 wherein providing the interrogator to the consumer comprises providing a software application capable of being executed on a programmable electronic device.

6. The method of claim 5 wherein the programmable electronic device comprises a wireless communication device and wherein the software application provided to the consumer enables the wireless communication device to wirelessly communicate with the system.

7. The method of claim 5 wherein the programmable electronic device communicates with the system through a wired interface.

8. The method of claim 1 further comprising analyzing data from both the first laser-detector pair and the second laser-detector pair.

9. A method comprising:

hermetically sealing a consumable product in a container;

packaging the container before sale to a consumer, wherein said packaging comprises attaching a system including sensors, a processor and a memory to the container to monitor and store in the memory data on parameters of the consumable product, wherein the sensors include a first laser-detector pair and a second laser-detector pair, and wherein attaching said system includes:

affixing directly to an outer surface of a neck of the container a flexible wrap including the first laser-detector pair to pass laser light through a headspace inside the container to reflect from a first reflector affixed to the outer surface of the neck of the container opposite the first laser-detector pair to non-invasively sense parameters of the consumable product including Trichloroanisole (TCA) by gas chromatography; and affixing directly to a body of the container a flexible label including the second laser-detector pair to pass laser light through the consumable product in the container to reflect from a second reflector affixed to the outer surface of the body of the container opposite the second laser-detector pair to non-invasively sense parameters of the consumable product including one or more of dissolved concentrations of oxygen, carbon dioxide, sulfur dioxide or TCA; and providing to the consumer a software application capable of being executed on a programmable electronic device to communicate with the system to access the data on parameters of the consumable product, wherein at least one of the flexible label or the flexible wrap include the processor and the memory of the system.

10. The method of claim 9 wherein the programmable electronic device comprises a wireless communication device and wherein the software application provided to the consumer enables the wireless communication device to wirelessly communicate with the system.

11. A system to monitor and store data on parameters of a consumable product in a sealed container, the system comprising:

a first flexible substrate affixed directly to an outer surface of the container, the first flexible substrate including a first laser-detector pair in the first flexible substrate to pass laser light through the container to reflect from a first reflector affixed to the outer surface of the container opposite the first laser-detector pair to non-invasively sense parameters of the consumable product;

a cap attached to the container and electrically coupled to the first flexible substrate, the cap including a processor and a memory to monitor, analyze and store in the memory data on the parameters of the consumable product; and an interrogator to communicate with the cap to access the data on parameters of the consumable product stored in the memory.

12. The system of claim 11 wherein the first flexible substrate comprises a flexible label and is affixed to the container to pass laser light through a liquid inside the container to sense one or more of pH, oxygen, carbon dioxide, sulfur dioxide or Trichloroanisole (TCA).

13. The system of claim 11 wherein the first flexible substrate comprises a flexible wrap and is affixed to a neck of the container to pass laser light through a headspace inside the container to sense one or more of pH, oxygen, carbon dioxide, sulfur dioxide or Trichloroanisole (TCA) by gas chromatography.

14. The system of claim 13 further comprising a second flexible substrate affixed directly to the outer surface of the container and electrically coupled to the cap, wherein the second flexible substrate comprises a flexible label including a second laser-detector pair to pass laser light through a liquid inside the container to sense one or more of pH, oxygen, carbon dioxide, sulfur dioxide or Trichloroanisole (TCA).

15. The system of claim 11 wherein the cap further comprises a speaker to communicate to a consumer data on at least one parameter of the consumable product.

16. The system of claim 11 wherein the cap further comprises a buzzer to communicate to a consumer data on at least one parameter of the consumable product.

17. The system of claim 11 wherein the cap further comprises an alphanumeric display to communicate to a consumer data on at least one parameter of the consumable product.

18. The system of claim 11 wherein the cap further comprises a number of light emitting diodes (LEDs) to communicate to a consumer data on at least one parameter of the consumable product.

* * * * *